United States Patent [19]

Bjoerkman et al.

[11] Patent Number: 6,124,322
[45] Date of Patent: Sep. 26, 2000

[54] INTRAVENOUS FORM OF THALIDOMIDE FOR TREATING IMMUNOLOGICAL DISEASES

[75] Inventors: Sven Bjoerkman, Lund; Peter Hoeglund, Klagstorp; Tommy Eriksson, Bjaerred, all of Sweden

[73] Assignee: Gruenenthal GmbH, Aachen, Germany

[21] Appl. No.: 09/166,953

[22] Filed: Oct. 6, 1998

[30] Foreign Application Priority Data

Oct. 6, 1997 [DE] Germany .......................... 195 43 968

[51] Int. Cl.⁷ .................. A01N 43/40; A61K 31/445; C07D 401/00
[52] U.S. Cl. .............................................. 514/323
[58] Field of Search ............... 514/323; 546/200, 546/201

[56] References Cited

U.S. PATENT DOCUMENTS 5,385,901  1/1995  Kaplan et al. ................. 514/231.5
5,434,170  7/1995  Andrulis ........................ 514/323

FOREIGN PATENT DOCUMENTS

WO 92/14455
    A1    3/1992   WIPO .
WO 92/14455    9/1992   WIPO .
WO 95/17154    6/1995   WIPO .
WO 97/37988   10/1997   WIPO .

OTHER PUBLICATIONS

Osol, Editor of Remington's Pharmaceutical Sciences, p. 1261, Jun. 1976.

Heger et al., "Embryotoxic effects of thalidomide derivatives in the non–human promated callithrx jacchus. IV Teratogenicity of micrograms/kg doses of the EM12 enantiomers". teratogenesesis, Carcinogenesis, and Mutagenesis, 14'(3), pp. 115–122, 1999.

Krenn et al. (1993), "Improvements in Solubility and Stability of Thalidomide upon Complexation with Hydroxypropyl–beta–cyclodextrin". [Abstract]. *Chemical Abstracts* 118:11605, XP002089567.

*Primary Examiner*—Dwayne C. Jones
*Attorney, Agent, or Firm*—Evenson, McKeown, Edwards & Lenahan, P.L.L.C.

[57] ABSTRACT

An aqueous thalidomide solution which is suitable as a parenteral form of application of thalidomide, particularly as an intravenous form of application, for treating immunological diseases, and a method of producing the corresponding thalidomide solution.

3 Claims, No Drawings

INTRAVENOUS FORM OF THALIDOMIDE FOR TREATING IMMUNOLOGICAL DISEASES

BACKGROUND OF THE INVENTION

This invention relates to a parenteral form of application of thalidomide and to a method of producing it.

The excessive formation of the cytokinin TNF-a (tumour necrosis factor a) plays a central part in the pathogenesis of graft-versus-host syndrome, aphthous stomatitis, erythema nodosum leprosum, morbus Boeck, morbus Crohn, rheumatoid arthritis and a series of other diseases which are associated with inflammatory symptoms. The basis for the therapy of these diseases consists of the targeted suppression of the release of TNF-a, by administering immunomodulating active ingredients, such as dexamethasone or thalidomide for example. While injectable forms of corticoids such as dexamethasone exist, this has hitherto not been the situation for thalidomide.

In the treatment of aphthous stomatitis, thalidomide has been shown to be superior to classical immunosuppressants. Examples of diseases in which thalidomide has exhibited good efficacy without resulting in a general immunosuppression include cutaneous lupus erythematosus, pyoderma gangrenosum and orogenital ulcers with morbus Behcet, as well as ulcerations in HIV-infected patients, which do not differ histologically from aphthous ulcers and in which—in contrast to the majority of HIV-associated mucocutaneous lesions—no microbial instigators can be detected. As distinct from stomatitis aphthosa, these lesions, which can be characterized as major aphthae, can occur in the entire digestive tract, and when located in the pharyngeal space or the esophagus make the absorption of food difficult, and also make the taking of oral medication difficult, due to the pain which they cause. The pathogenetic factors are endogenous mediators which have effects on the endothelium and on circulating leukocytes. Under the influence of locally-formed TNF-a and other cytokinins, there is a marked increase in the adhesiveness of the endothelium in relation to leukocytes, which makes a definitive contribution to the development of venous vasculitis. Substances which, like thalidomide, suppress this alteration of the endothelium without at the same time blocking the specific cellular immune defense, can constitute an important advance in therapy.

In severe cases of pharyngeal or esophageal ulcers, in which the taking of oral medication is made difficult, or in which this may even be impossible, and in cases of HIV-associated pathology in which severe symptoms of diarrhoea make the use of oral medication unpredictable, it is appropriate to administer active ingredients parentally. However, the low solubility of thalidomide in water (0.012 mg/ml; Arch. Pharm. 321, 371 (1988)) constitutes an obstacle to the parenteral administration of this active ingredient. There has, therefore, been no lack of attempts to develop water-soluble forms of administration.

Water-soluble thalidomide derivatives are known from DE 4,211,812. These thalidomide derivatives have a considerably higher solubility in water than that of thalidomide and are suitable for parenteral administration.

In addition, thalidomide prodrugs have been proposed for parenteral application which can be administered in water-soluble form in the physiological pH range and which are toxicologically harmless (DE 19,613,976). A disadvantage here is that both types of the aforementioned compounds involve higher production costs than the costs for the production of thalidomide.

SUMMARY OF THE INVENTION

The underlying object of the present invention consisted of developing a water-soluble form of application of thalidomide.

Another object was to provide a form of application which would be stable in a form dissolved in water.

Yet another object was to provide a water-soluble form of thalidomide having non-physiological physicochemical properties which would not give rise to toxicological effects.

It has been found that under certain conditions the requirements imposed on the form of application to be developed can be fulfilled by the use of pure enantiomers of thalidomide. As used herein the term "pure enantiomer" refers to a -orm which contains less than 1% of its optical antipode.

The enantiomers of thalidomide have a solubility in water which is higher by a factor of 6 than that of the racemate. The production of aqueous solutions is not practicable, however, due to the tendency of thalidomide to undergo spontaneous hydrolysis. However, if the pH of aqueous solutions falls within a pH range which is less than or equal to 5.5, hydrolysis does not occur.

According to the current state of knowledge, it is not possible to associate a defined isomer with the mode of action of thalidomide against immunological diseases. Pure enantiomers of thalidomide are converted back into the racemate in vitro and in vivo. Therefore, the antipode is also formed immediately after the parenteral administration of one of the isomers of thalidomide in vivo. An equilibrium is established after about 4 hours.

The present invention accordingly relates to a solution, which is suitable for parenteral application, of one of the two thalidomide enantiomers

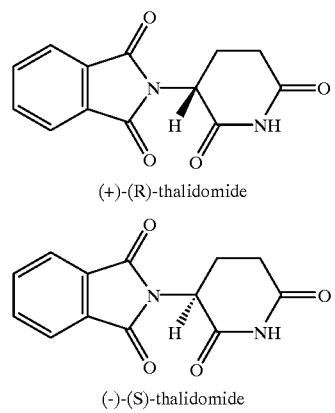

(+)-(R)-thalidomide (-)-(S)-thalidomide wherein this solution is an aqueous solution with a pH less than or equal to 5.5 and contains glucose as a constituent. According to the invention, one of the two thalidomide enantiomers is dissolved in isotonic glucose solution. The definition of the invention comprises both solutions of (+)-(R)-thalidomide and solutions of (−)-(S)-thalidomide, which can be used individually or alternatively for parenteral application, particularly for intravenous administration.

Suitable injectable forms of application of thalidomide are those which have a content of active ingredient of at least 0.2 mg/ml.

The present invention further relates to a method of producing the aqueous thalidomide solution. According to this aspect of the invention, (+)-(R)-thalidomide or (−)-(S)- thalidomide is added in pure form to an isotonic glucose solution with a pH of 4 to 5, and this mixture is shaken until complete dissolution of the respective thalidomide enantiomer has occurred, is subsequently treated with ultrasound and is filtered under aseptic conditions.

The form of application according to the invention is toxicologically harmless for both rapid and slow infusion (10 ml/min).

Pharmaceutical compositions according to the invention comprise glucose in addition to one of the enantiomers of thalidomide. Other adjuvant substances may optionally be added to the thalidomide solution. The choice of these further adjuvant substances and the amounts to be used depend on exactly how the pharmaceutical composition is to be administered.

The amount of active ingredient to be administered to the patient, which depends on the weight of the patient, on the type of parenteral administration, on the indication and on the degree of severity of the illness, is usually between 0.1 and 1 mg/kg.

EXAMPLES

Example 1

In order to produce an infusion solution in a concentration of 200 µg/ml, 70 mg (+)-(R)-thalidomide in 350 ml of a 5% glucose solution for infusions (pH 4 to 5) were introduced into a glass infusion bottle. The mixture was thoroughly shaken and treated for 15 minutes with ultrasound. Since the dissolved thalidomide concentration depends on the intensity of shaking and of the ultrasound treatment, both steps were repeated until complete dissolution was achieved. The water temperature in the ultrasonic bath reached a maximum of 33° C. The solution was filtered under aseptic conditions through a Millex GS sterile filter with a pore size of 0.22 µm (Millipore S. A., Molsheim, France) into a sterile glass infusion bottle. The solution was stored at room temperature. The pH of the final solution was 5.5.

The duration of the ultrasound treatment can be reduced by using a solution of the pure enantiomer in ethanol. This has an initial concentration which is higher by a factor of 5 to 10.

Example 2

In order to produce an infusion solution in a concentration of 200 µg/ml, 70 mg (−)-(S)-thalidomide in 350 ml glucose solution for infusions (pH 4 to 5) were introduced into a glass infusion bottle. The procedure employed was as in Example 1. The pH of the final solution was 5.5.

Stability Testing

Portions for analysis were removed daily from the solutions on 10 successive days. After 10 days, the respective thalidomide enantiomers were still completely intact, without hydrolysis having occurred. After this period of time, the thalidomide enantiomers contained less than 1% of their optical antipodes.

The foregoing description and examples have been set forth merely to illustrate the invention and are not intended to be limiting. Since modifications of the disclosed embodiments incorporating the spirit and substance of the invention may occur to persons skilled in the art, the invention should be construed broadly to include all variations falling within the scope of the appended claims and equivalents thereof.

What is claimed is:

1. An aqueous thalidomide solution comprising a pure enantiomer of thalidomide selected from the group consisting of (+)-(R)-thalidomide and (−)-(S)-thalidomide, dissolved in an isotonic glucose solution, said thalidomide solution having a pH of at most 5.5.

2. An aqueous thalidomide solution according to claim 1, wherein said thalidomide solution contains at least 0.2 mg/ml of said pure enantiomer of thalidomide.

3. A method of producing an aqueous thalidomide solution, said method comprising the steps of:

adding a pure enantiomer of (+)-(R)-thalidomide or (−)-(S)-thalidomide to an isotonic glucose solution with a pH of 4 to 5;

shaking the resulting mixture until complete dissolution of the respective thalidomide enantiomer has occurred;

treating the thalidomide solution with ultrasound, and filtering the thalidomide solution under aseptic conditions.

* * * * *